United States Patent [19]

von Plessen et al.

[11] Patent Number: 4,916,257

[45] Date of Patent: Apr. 10, 1990

[54] PROCESS FOR THE PURIFICATION OF 2-HYDROXYNAPHTHALENE-6-CARBOXYLIC ACID

[75] Inventors: Helmold von Plessen, Königstein; Siegbert Rittner, Mörfelden-Walldorf; Heinrich Volk, Bad Vilbel; Werner Wykypiel, Rodgau; Rudolf Neeb, Offenbach, all of Fed. Rep. of Germany

[73] Assignee: Hoechst Aktiengesellschaft, Frankfurt am Main, Fed. Rep. of Germany

[21] Appl. No.: 296,441

[22] Filed: Jan. 12, 1989

[30] Foreign Application Priority Data

Jan. 15, 1988 [DE] Fed. Rep. of Germany ....... 3800989

[51] Int. Cl.$^4$ ............................................. C07C 63/34
[52] U.S. Cl. ...................................... 562/467; 562/425
[58] Field of Search ......................... 562/467; 582/425

[56] References Cited

U.S. PATENT DOCUMENTS

| | | | |
|---|---|---|---|
| 1,593,816 | 7/1926 | Andre | 562/467 |
| 2,287,864 | 6/1942 | Burton et al. | 562/467 |
| 4,057,576 | 11/1977 | Bachmann | 562/467 |
| 4,287,357 | 9/1981 | Mueller et al. | 562/425 |
| 4,374,262 | 2/1983 | McGinnis | 562/467 |
| 4,393,191 | 7/1983 | East | 528/207 |

FOREIGN PATENT DOCUMENTS

| | | |
|---|---|---|
| 0053824 | 6/1982 | European Pat. Off. . |
| 0081753 | 11/1985 | European Pat. Off. . |
| 436524 | 8/1924 | Fed. Rep. of Germany . |
| 2446450 | 4/1981 | France . |
| 0257815 | 9/1926 | United Kingdom . |
| 2174706 | 11/1986 | United Kingdom . |

OTHER PUBLICATIONS

Beilstein, 4th Edition, vol. 10, IV/2 (1983), p. 1994.

*Primary Examiner*—Paul J. Killos

[57] ABSTRACT

The invention relates to a process for purification of 2-hydroxynaphthalene-6-carboxylic acid by recrystallization. In this process, the crude acid is recrystallized from water-miscible linear or cyclic aliphatic ethers, aliphatic polyethers or aliphatic hydroxy ethers or from at least 10% strength by weight aqueous solutions of these ethers. Recrystallization from a 35–90% strength by weight aqueous solutions of 1,4-dioxane is particularly preferred.

9 Claims, No Drawings

PROCESS FOR THE PURIFICATION OF 2-HYDROXYNAPHTHALENE-6-CARBOXYLIC ACID

DESCRIPTION

The invention relates to a process for the purification of 2-hydroxynaphthalene-6-carboxylic acid (hereinafter also designated in short "2,6-acid") by recrystallization.

The 2,6-acid used for the preparation of special heat-resistant plastics as a monomer must have "fibre grade quality" for the polycondensation, that is, it must be very pure. However, this requirement is difficult to meet, since the crude product is produced according to a variation of the Kolbe-Schmitt reaction by reaction of the potassium salt of 2-naphthol with $CO_2$ (U.S. Pat. No. 1,593,816, U.S. Pat. No. 4,287,357, European Patent 0,081,753). In this reaction, significant amounts of decomposition products (tar and resins) are formed, which are just as difficult to separate off as the byproducts formed.

Until now the crude acid, after separating off 2-naphthol, was processed in an expensive manner, specifically by extraction, adsorption on carbon and dissolution in water and reprecipitation. How much the qualities obtained by this process leave to be desired, is illustrated by the commercial products which, instead of being colorless, are more or less brownish.

Surprisingly, it has now been found that 2,6-acid having the desired high purity can be produced by recrystallizing the crude acid from certain water-miscible ethers or aqueous solutions thereof.

The invention accordingly relates to a process for the purification of 2-hydroxynaphthalene-6-carboxylic acid by recrystallization, which comprises recrystallizing the crude acid from water-miscible linear or cyclic aliphatic ethers, aliphatic polyethers or aliphatic hydroxy ethers or from at least 10% strength by weight aqueous solutions of these ethers.

It is particularly advantageous that the treatment of the crude 2,6-acid using the ethers or their aqueous solutions also separates off critical impurities of 2,6-acid, such as 2-naphthalenesulfonic acid, 2-naphthol, 2-hydroxynaphthalene-3-carboxylic acid, 6-hydroxynaphthalene-2,7-dicarboxylic acid, 2,2'-dihydroxy-1,1'-dinaphthyl in addition to the coloring component.

One method of the crystallization process according to the invention consists in dissolving the crude 2,6-acid in the ethers mentioned or aqueous solutions thereof with heating and then allowing the purified acid to crystallize out by cooling. According to a different method, water is added to the solutions of the crude acid in the ethers mentioned in such an amount that crystallization sets in. Furthermore, it is possible to distill of such an amount of ether from the solutions of the crude acid in the ethers mentioned or their aqueous solutions that crystallization sets in.

Before the crystallization according to the invention, the crude 2,6 -acid is preferably freed from the major amount of any 2-naphthol present. For example, it is possible to distill off the 2-naaphthol formed as a byproduct in the reaction of the potassium salt of 2-naphthol with $CO_2$ at reduced pressure (for example 50–65 mbar) and elevated temperature (for example 260° C.) from the carboxylation melt.

The crystallization of 2,6-acid can be carried out either at room temperature or at elevated (up to the boiling point) or reduced temperatures (to about −20° C.). The crystallization is also possible at elevated pressure in combination with a corresponding increase in the boiling point.

The crystallization process according to the invention can be carried out either batchwise or continuously. Either crystallization by cooling or evaporation or the so-called vacuum crystallization can be used. It can be advantageous to carry out the crystallization under an inert gas atmosphere. A suitable inert gas is in particular nitrogen. In addition, carbon dioxide or argon can be used for this purpose.

For example, the following ethers or mixtures thereof can be employed in the process according to the invention, with or without the addition of water:

Monoethylene glycol dimethyl ether (1,2-dimethoxyethane)
Diethylene glycol dimethyl ether (2,2'-dimethoxydiethyl ether)
Triethylene glycol dimethyl ether (1,2-bis(2'-methoxyethoxy)ethane
Tetraethylene glycol dimethyl ether (mixture of homologues)
Diethylene glycol
Triethylene glycol
Polyethylene glycol, for example polyethylene glycol 400 (molecular weight 380–420)
Pentaethylene glycol dimethyl ether
Triethylene glycol methyl ethyl ether
Tetraethylene glycol methyl tert.-butyl ether
Monoethylene glycol monomethyl ether
Diethylene glycol monomethyl ether
Triethylene glycol monomethyl ether
Tetraethylene glycol monomethyl ether
1,4-Dioxane
1,3,5-Trioxane
Trioxepane
Tetroxane
Bicyclotetroxane
Dimethylbicyclotetroxane
Methyldicyclotetroxane
Water-soluble short-chain ethylene oxide/propylene oxide copolymers
2-Methoxy-1-butanol
Glycerol monomethyl ether
Glycerol dimethyl ether
Glycerol trimethyl ether.

Preferably, 1,4-dioxane or an at least 10% strength by weight aqueous solution of one of the following ethers is employed: 1,4-dioxane, diethylene glycol, triethylene glycol, polyethylene glycol or ethylene glycol dimethyl ether. At least 10% strength by weight aqueous solutions of 1,4-dioxane or ethylene glycol dimethyl ether, but in particular the first mentioned solution, are particularly suitable. The 1,4-dioxane content of this solution should be in general 10–90% by weight, preferably 20–90% by weight, in particular 35–90% by weight. It is true that solutions having a 1,4-dioxane content of more than 90% by weight or anhydrous 1,4-dioxane are equally industrially suitable, but economically they are less favorable due to the higher amount of ether used for the same industrial effect. What applies to the aqueous solutions of 1,4-dioxane with respect to the ether contents of the solutions (in general 10–90, preferably 20–90, in particular 35–90, % by weight) and the suitability of the pure ethers equally applies to the aqueous solutions of ethylene glycol dimethyl ether and to the other ethers mentioned.

The great advantage of the process according to the invention is not only the high purifty of the 2,6-acid obtained by also the fact that the purification consists of only one basic engineering operation.

The high purity 2,6-acid produced represents a valuable product. For example, aromatic polyesters processable to give heat-resistant plastics or fibers (U.S. Pat. No. 4,393,191) can be prepared from it and p-hydroxybenzoic acid. Apart from serving as monomer for plastics, fibers and threads, the 2,6-acid can also serve as synthetic building block, for example for dyes or textile assistants.

The process according to the invention is illustrated by means of the following examples. The color number of the crude or purified 2,6-acid was determined aas follows:

1 g of 2,6-acid was dissolved in 80 ml of 100% strength acetic acid in an ultrasonic bath, and the solution was made up to 100 ml with 100% strength acetic acid. The absorption at 400 nm was then determined using a spectrophotometer. Each time the measurement took place within 2 hours, after the dissolution of the sample had been initiated. The color number at 400 nm was then calculated from the formula $$\text{Color No. (400 nm)} = \frac{\text{Absorption at 400 nm}}{(1 \text{ cm}) \times \text{concentration of the sample in ppm}}$$

1 g per 100 ml being calculated as 10,000 ppm. In Examples 1–10, the crude 2,6-acid always has the color number $25.6 \times 10^{-6}$ and in Example 11 it had the color number $61.2 \times 10^{-6}$.

EXAMPLE 1

12.5 g of crude 2,6-acid were stirred with 100 ml of water and dissolved with the addition of 40 ml of ethylene glycol dimethyl ether and heating. After the solution had been treated with 2.5 g of activated carbon and filtration, crystals precipitated upon cooling, which were filtered off. The substance obtained was then recrystallized from 150 ml of 35% strength by volume ethanol. After drying, 8.0 g of crystallene 2,6-acid were obtained: Melting point 246°–247.5° C., color number $5.3 \times 10^{-6}$.

EXAMPLE 2

10 g of crude 2,6-acid was dissolved in a mixture of 100 ml of water and 45 ml of diethylene glycol with heating.

The solution was refluxed for 30 minutes in the presence of 0.16 g of activated carbon and subsequently filtered. The product crystallizing from the solution was filtered off and washed with water. After drying, a color number of $10.7 \times 10^{-6}$ was obtained.

EXAMPLE 3

25 g of crude 2,6-acid were heated with 200 ml of water with stirring and dissolved by the addition of 150 ml of 1,4-dioxane. After treatment with 5 g of activated carbon, the solution was cooled and the crystallized 2,6-acid recovered and washed with a mixture of 100 parts by volume of water and 60 parts by volume of 1,4-dioxane. The crystals were recrystallized from 200 ml of 35% strength by volume ethanol and washed.

After drying, the yield was 18 g of colorless crystals. THe melting point was 247°–248.5° C. and the color number $1.4 \times 10^{-6}$. Impurities (in % by weight): 2-naphthalenesulfonic acid less than 0.002%; 2-hydroxynaphthalene-3-carboxylic acid less than 0.05%; 2-naphthol less than 0.05%; 6-hydroxynaphthalene-2,7-dicarboxylic acid 0.05%; 2,2′-dihydroxy-1,1′-dinaphthyl less than 0.05%.

The crude 2,6-acid had the following impurities (in % by weight): 2-naphthalenesulfonic acid less than 0.002%; 2-hydroxynaphthalene-3-carboxylic acid 0.227%; 2-naphthol 0.065%; 6-hydroxynaphthalene-2,7-dicarboxylic acid 0.421%; 2,2′-dihydroxy-1,1′-dinaphthyl 0.018%.

EXAMPLE 4

12.5 g of crude 2,6-acid were dissolved in 100 ml of water and 55 ml of diethylene glycol with heating. After treating the hot solution for 13 minutes with 1 g of activated carbon, it was filtered. Crystals which precipitated in the filtrate were again dissolved by heating. The product was then allowed to crystallize slowly. After filtration, the crystals were washed with 25% strength by volume ethanol. Yield after drying: 9.7 g.

The product recrystallized from 120 ml of 35% strength by volume ethanol had a color number of $9.2 \times 10^{-6}$.

EXAMPLE 5

12.5 g of crude 2,6-acid were dissolved in 100 ml of water and 75 ml of 1,4-dioxane with heating. After treatment of the solution with 2.5 g of activated carbon and filtration, 11.9 g of 2,6-acid having a color number of $3.4 \times 10^{-6}$ crystallized from the solution.

EXAMPLE 6

12.5 g of crude 2,6-acid were dissolved in 100 ml of water and 40 ml of ethylene glycol dimethyl ether with heating, and the solution was treated with 2.5 g of activated carbon. The filtered solution was then cooled for the purpose of crystallization. The crystals which were washed with a small amount of dilute ethanol were then recrystallized again from a mixture of water and ethylene glycol dimethyl ether of the above composition. Yield: 8.1 g, color number $8.5 \times 10^{-6}$.

EXAMPLE 7

12.5 g of crude 2,6-acid were dissolved in 100 ml of water and 50 ml of 1,3-dioxolane with heating. After treatment with 2.5 g of activated carbon, the solution was filtered, cooled and the crystals were recovered. Recrystallization from 120 ml of 35% strength by volume ethanol gave a yield of 7.3 g. Melting point: 246°–247.9° C., color number: $7.8 \times 10^{-6}$.

EXAMPLE 8

12.5 g of crude 2,6-acid were dissolved in 100 ml of water and 50 ml of 1,3-dioxolane with heating and treated with 2.5 g of activated carbon. The crystals were filtered off from the cooled solution, washed with 35% strength by volume ethanol and again dissolved in 100 ml of water and 50 ml of 1,3-dioxolane and recrystallized therefrom. Yield: 5.1 g, color number: $6.8 \times 10^{-6}$.

EXAMPLE 9

12.5 g of crude 2,6-acid were dissolved with heating in 180 ml of 1,4-dioxane. After treatment of the solution with 2.5 g of activated carbon, filtration and cooling, 9.1 g of crystallized 2,6-acid were recovered from the solution. Recrystallization from 100 ml of 35% strength by volume ethanol and washing of the crystals with the same solvent gave, after drying, a yield of 6.7 g. The color number was $3.3 \times 10^{-6}$.

EXAMPLE 10

25 g of crude 2,6-acid were dissolved in 96 ml of dioxane and 24 ml of water with stirring and heating. After treatment with 1 g of activated carbon, filtration and cooling, the solution gave crystallized 2,6-acid, which was filtered off and washed with 25% strength by volume ethanol. After drying, the yield was 18.2 g and the color number $3.6 \times 10^{-6}$.

EXAMPLE 11

25 g of crude 2,6-acid (color number $61.2 \times 10^{-6}$) were dissolved in 200 ml of water and 150 ml of dioxane with stirring and heating. After treatment with 2 g of activated carbon and filtration, the solution upon cooling gave crystals which were separated off and washed with 25% strength by volume ethanol. The product was again recrystallized from 180 ml of water and 135 ml of dioxane, while being treated with 1 g of activated carbon. After washing with 25% strength by volume ethanol and drying, 21.5 g of purified 2,6-acid having a color number of $2.7 \times 10^{-6}$ were obtained.

What is claimed is:

1. A process for the purification of 2-hydroxynaphthalene-6-carboxylic acid by recrystallization, which comprises recrystallizing the crude acid from water-miscible linear or cyclic aliphatic ethers, aliphatic polyethers or aliphatic hydroxy ethers or from at least 10% strength by weight aqueous solutions of these ethers.

2. The process as claimed in claim 1, wherein the recrystallization is carried out from a 20–90% strength by weight aqueous solution of ethylene glycol dimethyl ether.

3. The process as claimed in claim 1, wherein the recrystallization is carried out from a 20–90% strength by weight aqueous solution of 1,4-dioxane.

4. The process as claimed in claim 1, wherein the recrystallization is carried out from a 20–90% strength by weight aqueous solution of diethylene glycol.

5. The process as claimed in claim 1, wherein the recrystallization is carried out from a 20–90% strength by weight aqueous solution of triethylene glycol.

6. The process as claimed in claim 1, wherein the recrystallization is carried out from a 20–90% strength by weight aqueous solution of polyethylene glycol.

7. The process as claimed in claim 1, wherein the recrystallization is carried out from a 35–90% strength by weight aqueous solution of ethylene glycol dimethyl ether.

8. The process as claimed in claim 1, wherein the recrystallization is carried out from a 35–90% strength by weight aqueous solution of 1,4-dioxane.

9. The process as claimed in claim 1, wherein the recrystallization is carried out from an at least 90% strength by weight aqueous solution of 1,4-dioxane or from anhydrous 1,4-dioxane.

* * * * *